United States Patent [19]
Andreiko et al.

[11] Patent Number: 5,618,176
[45] Date of Patent: Apr. 8, 1997

[54] ORTHODONTIC BRACKET AND LIGATURE AND METHOD OF LIGATING ARCHWIRE TO BRACKET

[75] Inventors: Craig A. Andreiko, Alta Loma; Mark A. Payne, Whittier, both of Calif.

[73] Assignee: Ormco Corporation, Glendora, Calif.

[21] Appl. No.: 489,501

[22] Filed: Jun. 12, 1995

[51] Int. Cl.[6] .................................................. A61C 7/00
[52] U.S. Cl. ................................ 433/11; 433/13; 433/10
[58] Field of Search .................................... 433/11, 13, 15, 433/17, 10, 21, 14

[56] References Cited

U.S. PATENT DOCUMENTS

| | | | |
|---|---|---|---|
| 3,043,006 | 7/1962 | Wallshein | 433/11 |
| 3,091,857 | 6/1963 | Rubin et al. | 433/11 |
| 4,074,433 | 2/1978 | Nelson | 433/21 |
| 4,149,314 | 4/1979 | Nonnenmann. | |
| 4,193,195 | 3/1980 | Merkel et al. | 433/13 |
| 4,371,337 | 2/1983 | Pletcher | 433/10 |
| 4,427,381 | 1/1984 | Hall | 433/14 |
| 4,492,573 | 1/1985 | Hanson | 433/11 |
| 4,496,318 | 1/1985 | Connelly, Jr. | 433/14 |
| 4,565,526 | 1/1986 | Kawata et al. | 433/8 |
| 4,725,229 | 2/1988 | Miller | 433/11 |
| 4,786,252 | 11/1988 | Fujita | 433/10 |
| 5,094,614 | 3/1992 | Wildman | 433/14 |
| 5,123,838 | 6/1992 | Cannon | 433/14 |
| 5,224,858 | 7/1993 | Hanson | 433/10 |
| 5,275,557 | 1/1994 | Damon | 433/10 |
| 5,362,233 | 11/1994 | Thompson | 433/9 |

Primary Examiner—Cary E. O'Connor
Attorney, Agent, or Firm—Wood, Herron & Evans, P.L.L.

[57] ABSTRACT

An orthodontic bracket and ligature are provided in which the bracket, in the preferred embodiment, includes a cylindrical post, spaced from a bracket base to extend horizontally parallel thereto, and having an archwire slot therein. A spring material ligature band, naturally coiled and secured to a plastic installation strip, is pulled around the post of the bracket until a hooked trailing terminal end of the band catches on the bracket, pulling it loose from the strip, and allowing it to snap around the post to hold and confine the archwire in the slot. Different width ligatures seat to different positions on the post to allow the wire to be held to selected tightnesses in the slot by selection of the ligature.

16 Claims, 3 Drawing Sheets

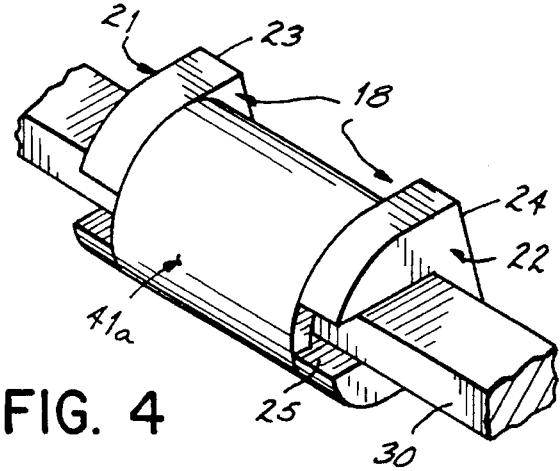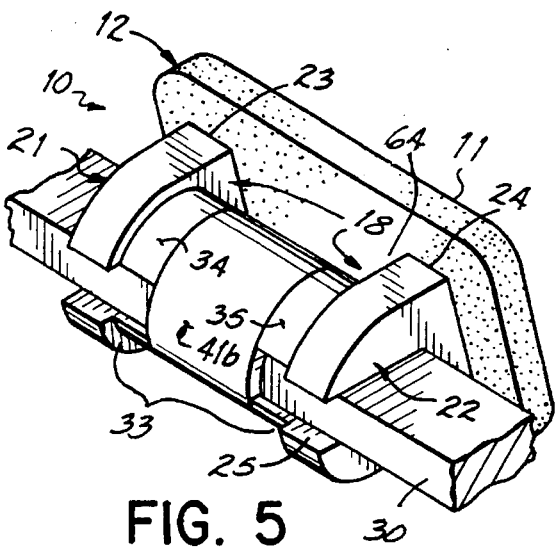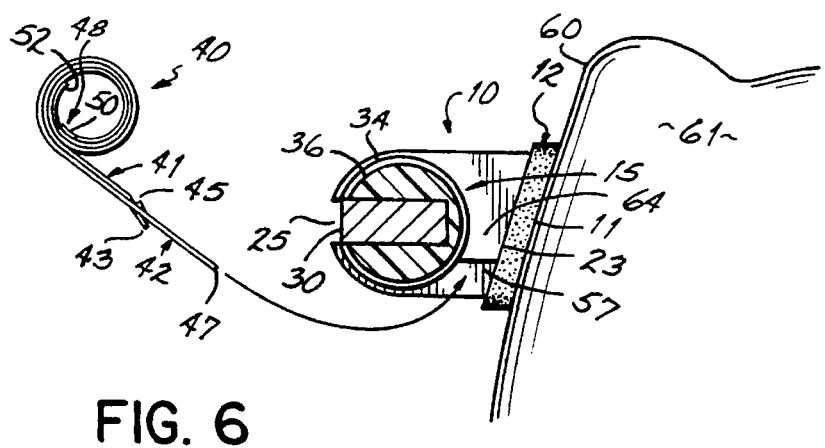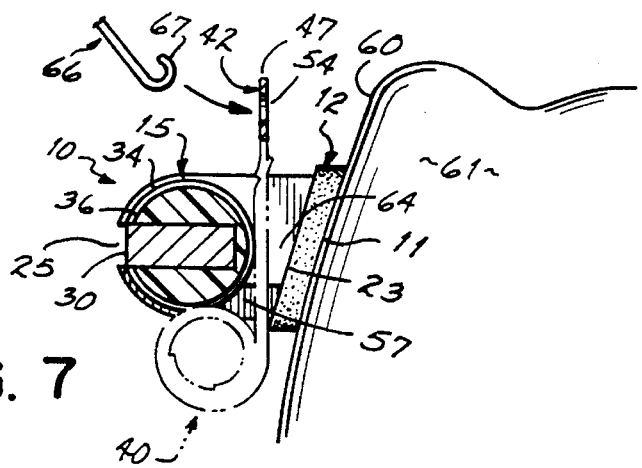

ORTHODONTIC BRACKET AND LIGATURE AND METHOD OF LIGATING ARCHWIRE TO BRACKET

The present invention relates to the design and use of orthodontic appliances for straightening teeth, and more particularly to formation of connections between orthodontic archwires and orthodontic brackets that are mounted on a patient's teeth.

BACKGROUND OF THE INVENTION

For decades, orthodontic appliances for use in the straightening of a patient's teeth have, for a given dental arch, been formed of an elastic metal orthodontic archwire and a plurality of orthodontic brackets, each secured to one of the patient's teeth and to which the archwire is connected. Typically, an orthodontic bracket standard in the field has included a base, or pad, that is secured to the tooth and an archwire support, fixed to the pad and containing an archwire slot, of rectangular cross-section, into which the archwire is fit.

Prior to the 1960s, orthodontic archwires had been literally ligated or tied to the brackets, usually with a strong though plastically bendable wire. The ligating of the wire to the brackets involved the meticulous manipulation of the fine wire by the orthodontist using a pliers, and then the cutting of the ligature wire, and the tieing of the ends of the wire so as to securely attach the archwire to the bracket and so as to prevent the sharp wire ends from injuring the patient. Because of the unpleasantness to the orthodontist and the patient of the ligating process, orthodontists have, for many years, desired a "ligatureless bracket" that would replace the ligating process.

True ligatureless brackets have been envisioned as brackets with reusable, non-removable spring clips of one sort or another to fix the archwire to the brackets. In their implementation, true ligatureless brackets have not been successful in performance or in the marketplace for several reasons, most relating to unsatisfactory clinical function, reliability and technique modifications that these brackets require.

Since the 1960s, a urethane doughnut or O-ring like ligature has had widespread acceptance. Such a ligature is radially expanded with a plier tool and snapped around four hooked ends of the tie wings of a double winged bracket and over an archwire set in the slot of the bracket, thereby tightly urging the archwire into the bracket slot and ligating the archwire to the bracket. While not totally eliminating the ligature, the urethane doughnut performed the function of the former ligature without requiring the twisting, cutting or tucking-in of the sharp ends of the ligating wire.

Nonetheless, the current urethane doughnut ligature and double tie-wing bracket is less than totally ideal in several respects. First, in many applications the tie-wings of the brackets interfere with occlusion. Further, they have a limited latitude of placement on the teeth, leave a great deal of room for improvement in aesthetic appearance, and present moderate difficulty in maintaining hygiene. Additionally, differences in designs of the tie-wing brackets for different teeth of a patient can require the orthodontist to stock and match ligatures of different sizes and properties to respective individual brackets. Therefore, there is a need for improvement in the art of ligating orthodontic archwires to brackets and in the overall design of the brackets and the archwire securing structure.

SUMMARY OF THE INVENTION

A primary objective of the present invention is to provide a better method for securing an orthodontic archwire to a patient's teeth. A further objective of the present invention is to provide a orthodontic appliance component for supporting an orthodontic archwire on the teeth of a patient that will overcome the shortcomings of the prior art. More particular objectives of the present invention are to provide an orthodontic bracket and a bracket-to-archwire ligature that improves upon the state of orthodontic appliances, to provide a method of ligating orthodontic archwires to brackets that improves upon the state of the practice of orthodontics, and to provide an orthodontic bracket and a bracket-to-archwire ligature that is strong and truly elastic, is easy to use and can be installed rapidly, provides little interference with occlusion and enhanced latitude in placement, improves hygiene, is an aesthetic improvement over conventional brackets and ligatures, and can be made to common geometry for all teeth.

According to the principles of the present invention, there is provided an orthodontic bracket and an orthodontic bracket-to-archwire ligature of cooperating geometry. The bracket includes a bracket base securable to a tooth and a cylindrical post-like member supported in spaced relationship with the interface of the base with the tooth and having an archwire slot therein extending nominally parallel to the axis of the cylindrical post. The ligature is configured to encircle the post to confine the archwire in the slot.

In the preferred embodiment of the invention, the bracket includes a support formed preferably by a pair of spaced parallel end plates or legs with the cylindrical post extending therebetween. The legs are provided either with a foot portion that forms part of the bracket base configured to bond directly to the crown surface of a tooth, or preferably, are to a pad portion that is configured to bond to the tooth. Installed on a tooth, the legs are nominally oriented vertically with the post extending horizontally and generally mesial-distally approximately parallel to the archwire of the appliance.

Further, in the preferred embodiment, the ligature is formed of a flat strip of spring metal shaped, in its unstressed state, in a coil of diameter smaller than that of the post of the bracket for which it is suited, so that, when wrapped around the post, it exerts radially inward force against the post to hold the archwire in the slot.

The slot of the bracket may be configured to allow the wire to slide in the slot by providing space between the wire and the ligature when the wire is seated on the bottom of the slot, or so that the wire fills the slot from the slot bottom to the surface of the ligature and thereby be held more tightly in the slot. Alternatively, the slot of the bracket may be dimensioned to allow the wire to slide, with space maintained between the wire and the ligature, and to also be held tightly with a spacer between the wire and the ligature. The spacer may be fixed to the ligature.

The ligature, in its preferred form, is provided to the orthodontist separate from the bracket, in coiled form and in combination with a disposable installation strip. The strip of this preferred embodiment is provided with a leading end that is insertable between the post and the base of the bracket, after the archwire is positioned in the bracket slot with the bracket mounted on the tooth, to serve as a handle by which the ligature can be pulled by the orthodontist, with the hooked end of an appropriate tool, for example. The ligature is removably secured to the strip so that it remains wrapped around the post after the strip is pulled around the post.

Preferably the ligature is provided with tabs at its trailing end that catch on a shoulder on the bracket legs to facilitate pulling of the installation strip free of the ligature to leave the ligature in position around the bracket post with the archwire tied in the slot. Additionally, the preferred ligature is provided in a plurality of different widths, and the outer surface of the post of the bracket is stepped so that ligatures of different widths will seat at different radii around the post and thereby confine the wire at different depths within the slot. Thus, by selection of different ligatures in the course of the treatment, the orthodontist can change the tightness with which the wire is held to the bracket, without changing the bracket.

The present invention provides an improved orthodontic bracket, an improved bracket-to-archwire ligature, and an improved method of securing an archwire to the teeth of a patient in the installation of an orthodontic appliance. A primary objective of the present invention is to provide a better method for securing an orthodontic archwire to a patient's teeth. The invention overcomes shortcomings of the prior art, particularly providing a bracket-to-archwire ligature that is strong and truly elastic, is easy to use and can be installed rapidly. Further, the ligated bracket according to the present invention provides little interference with occlusion, has enhanced latitude in placement, improves hygiene, and is an aesthetic improvement over conventional brackets and ligatures of the prior art, thus enhancing its acceptability to patients. Additionally, the bracket of the present invention can be made to common geometry for all teeth.

These and other objectives and advantages of the present invention will be more readily apparent from the following detailed description of the drawings and preferred embodiments, in which:

BRIEF DESCRIPTION OF THE DRAWINGS

FIG. 4 is a perspective view of a portion of an orthodontic appliance illustrating a ligature and bracket assembly formed of the bracket and ligature of FIGS. 1 and 2 with an archwire secured thereto.

FIG. 5 is a perspective view, similar to FIG. 4, but illustrating a ligature of alternative dimensions forming an assembly with an alternative form of bracket of FIG. 1 in a configuration for holding the an archwire more tightly thereto.

FIG. 6 is a side elevational view, partially in cross section, showing a first step of the preferred embodiment of the method of the invention for ligating an archwire to the bracket.

FIG. 7 is a side elevational view, similar to FIG. 6, showing a second step of the preferred embodiment of the method of the invention for ligating an archwire to the bracket.

DETAILED DESCRIPTION OF THE PREFERRED EMBODIMENTS

Figure 1:
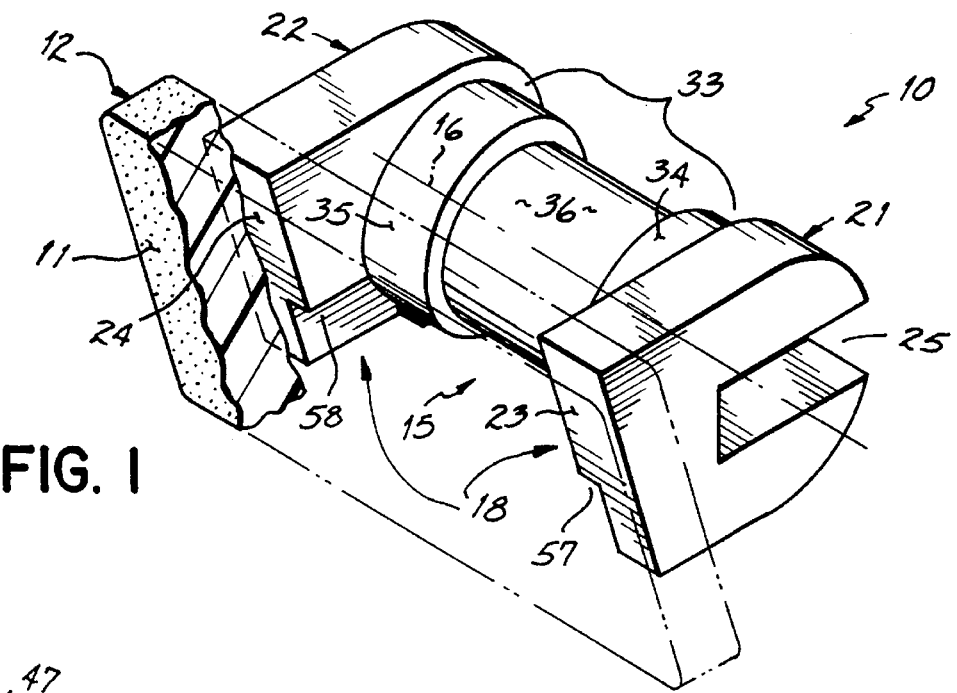
FIG. 1 is a rear perspective view of an orthodontic bracket according to one preferred embodiment of the present invention showing the bracket from the side that attaches to the tooth.

Referring to FIG. 1, an orthodontic bracket 10 according to one preferred embodiment of the present invention is illustrated. The bracket 10 has a base 11 in the form of a mounting surface to be secured to the crown surface of the tooth of a patient, usually by bonding with special orthodontic appliance adhesive. The base 11 is preferably formed on a bracket pad 12 (shown partially broken away) that generally rectangular in shape. The base mounting surface 11 is conventionally provided with a mesh laminate (not shown) to facilitate the adhesion of bonding of the mounting surface 11 to the crown surface of a tooth.

The bracket 10 is provide with a cylindrical post 15 that is rigidly supported relative to the pad 12 such that it is maintained in a fixed spaced relationship to the surface of the tooth on which the bracket 10 is mounted. The post 15 is preferably cylindrical and is supported relative to the base 11 such that its axis 16 is aligned horizontally with what may be defined as the longitudinal dimension of the post 15. The post has a transverse dimension defining the thickness of the post 15, which in the preferred embodiment is the diameter of the cylinder. When the mounting surface 11 of the bracket 10 is bonded to a tooth, the axis 16 of the post 15 is approximately parallel to the crown surface of the tooth to which the bracket 10 is attached.

The bracket 10 is provided with a support 18 which maintains the post 15 in its spaced relationship with the pad 12. In the illustrated embodiment, the support 18 is made up of a pair of spaced legs 21 and 22. The opposite ends of the post 15 are rigidly connected to the legs 21 and 22 such that the post 15 extends horizontally between the legs 21 and 22. Each of the legs 21 and 22 has a respective foot 23 and 24 which are rigidly attached to the pad 12. Alternatively, the bracket may be formed without the separate pad 12, in which case the mounting surface or base 11 of the bracket 10 is formed directly on the surfaces of the feet 23 and 24.

In the post 15 is formed an archwire slot 25 that is of rectangular cross-section to receive an archwire, e.g. 30 (FIGS. 4 and 5), usually also of rectangular cross-section. The slot 25 is formed in the post 15 on the side thereof that faces away from the base 11, parallel to the axis 16 of the post 15. The slot 25 also continues through the legs 21 and 22 of the support 18 to receive the archwire 30.

The outer surface of the post 15 constitutes a ligating surface 33 about which a ligature may be tied to secure the archwire 30 in the slot 25 of the bracket 10. This surface is generally cylindrical such that a ligature wound around it will generally form a circle and will confine an archwire 30 in the slot 25 of the bracket 10. Preferably, the ligating surface 33 of the post 15 is configured to permit an archwire 30 to be held in the slot 25 to differing degrees of tightness, or to hold wires of different thickness to the same or different tightnesses. To facilitate this selection of ways of ligating the wire to the bracket 10, the ligating surface 33 is preferably stepped, having a pair of larger diameter surface portions 34,35 adjacent the legs 21, 22, and a central smaller diameter portion 36 between the portions 34,35.

Figure 2:
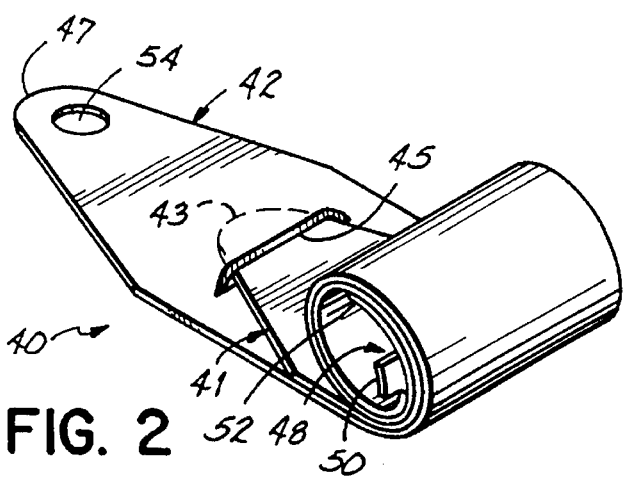
FIG. 2 is a perspective view of a ligature, according to a preferred embodiment of the invention, for attaching an archwire to the bracket of FIG. 1.
Figure 3:
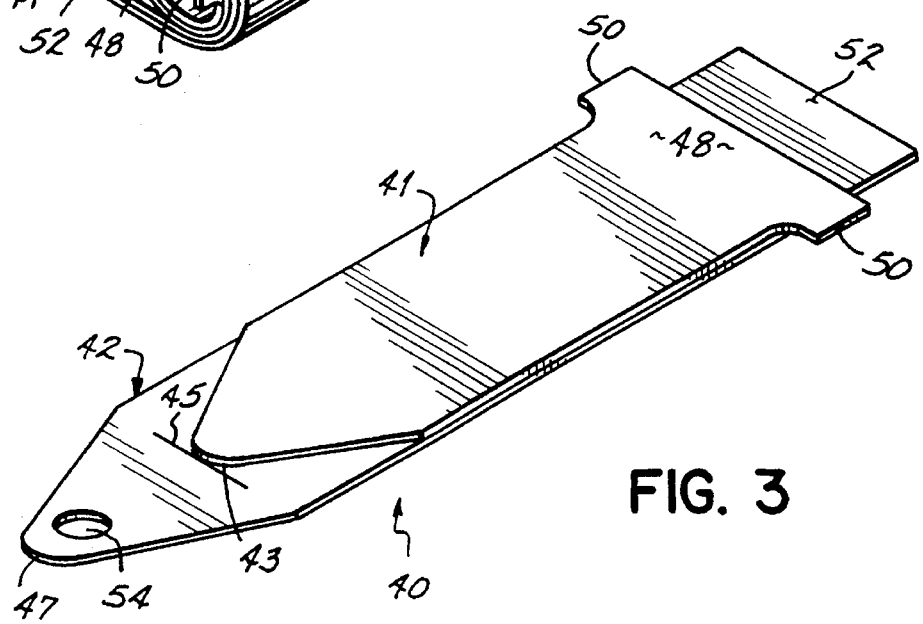
FIG. 3 is a perspective view similar to FIG. 2 showing the ligature uncoiled.

To tie the archwire 30 to the bracket 10 a specially configured ligature 40 is provided, as illustrated in FIGS. 2 and 3. The ligature 40 includes an elongated band 41 of a flat spring-like material, such as, for example, stainless steel or nickel-titanium alloy, that is preferably coated with a low friction material such as TEFLON™. The ligature 40 is shown in FIG. 2 with the band 41 in an unstressed condition, in which it assumes a coiled shape of generally circular form with a diameter less than that of the portion 34,35 or 36 of the cylindrical surface 33 of the post 15 on which it is designed to be wound.

The ligature 40 also includes a removable and disposable elongated installation strip 42 to which the band 41 is removably secured, such as with a forward end 43 thereof being inserted into a slot 45 in or near a leading end 47 of the strip 42. The band 41 is attached to the strip 42 such that, when the band 41 is coiled, the strip 42 lies on the outside of the band 41. The strip 42 is formed of a plastic material such as MYLAR™. With this arrangement, the band 41 coils to a slightly smaller diameter, causing the forward end 43 of the band 41 to urge forward into the slot 45. On the other hand, when the ligature 40 is laid flat, as illustrated in FIG. 3, the forward end 43 of the band 41 tends to move rearwardly away from leading end 47 of the strip 42.

As illustrated in both FIGS. 2 and 3, the band 41 has a terminal end 48 that is hooked. The hooked terminal end 48 is formed by a pair of tabs 50 projecting sidewardly from the terminal end 48 of the band 41, formed integrally of the spring-like material of which the band 41 is made. The band 41 is preferably, but not necessarily, shorter than the strip 42, such that then the band 41 and strip 42 are assembled with the forward end 43 of the band 41 in the slot 45, the strip 42 has a trailing end 52 that extends beyond the terminal end 48 of the band 41. The strip 42 is also provided with a hole 54 in the leading end 47 thereof that serves as a handle by which the strip 42, and the assembled ligature 40 that includes the band 41 attached to the strip 42, can be pulled with the use of a tool having a hooked end, or by a short piece of cord that may be tied to the strip 42 through the hole 54.

Preferably, the bands 41 are provided in a plurality of widths for use with the same bracket 10. In the illustrations, the plurality is two. A band 41a of the first width is illustrated in FIG. 4, wound about the ligating surface 33 of the post 15 such that it rests on the larger diameter portions 34,35 of the surface 33. With such a ligature, a larger wire 30 may be held in the slot 25, or, alternatively, a smaller wire 30 may be loosely held in the slot 25. In FIG. 5, a band 41b of a second width narrower than the width of band 41a (FIG. 4) is shown wound to a smaller diameter around the center portion 36 of the ligating surface 33, whereby a smaller wire 30 may be held in the slot 25, or the same size wire 30 may be held more tightly than with the band 41a.

When the support 18 is in the form of the pair of legs 21,22, whatever the width of the band 41, the tabs 50 are dimensioned to extend to both sides of the ligating surface 33 such they will not fit between the legs 21 and 22, so as to form a stop that pulls the band 41 from the strip 42. To engage these tabs 50 and pull the band 41 from the strip 42, the support 18 is provided with a pair of shoulders 57,58 formed in the respective legs 21,22 near the feet thereof 23,24, respectively.

The structural elements of the bracket 10 and the ligature 40 interact to form a bracket and ligature assembly, a plurality of which cooperate to connect one or two orthodontic archwires 30 to the teeth of a patient to form an orthodontic appliance. The use of the assembly is preferably in accordance with the preferred method of the invention.

The preferred method of ligating an archwire 30 to a bracket 10, according to the present invention, is illustrated by the drawing sequence of drawings, FIGS. 6–9. In FIG. 6, a bracket 10 is shown bonded at the mounting surface 11 on the pad 12 thereof to a crown surface 60 of a tooth 61 of a patient, such that the post 15 of the bracket 10 is spaced from the pad 12, by the supports 21,22 (21 only shown) leaving a space 64 between the ligating surface 33 and the pad 12. Once the orthodontist has bonded all of the brackets 10 in their proper placement positions on the crown surfaces 60 of the teeth 61 of the patient, the orthodontist inserts an archwire 30 in the slots 25 of each of the brackets 10. Then the orthodontist ties the wire 30 to the brackets 10.

To tie the archwire 30 in the slot 25 of a bracket 10, the orthodontist takes a pre-assembled ligature 40 and inserts the leading end 47 of the strip 42 through the space 64 between the pad 12 and the post 15. The end 47 is inserted from the side of the bracket 10 on which the shoulders 57,58 are formed in the legs 21,22 of the support 18. Preferably, the bracket 10 is mounted on the teeth 61 such that the shoulders 57,58 are toward the patient's gum. The ligature so inserted is illustrated in FIG. 7, with the leading end 47 of the strip 42 projecting through the space 64, exposing the hole 54 therein.

Figure 8:
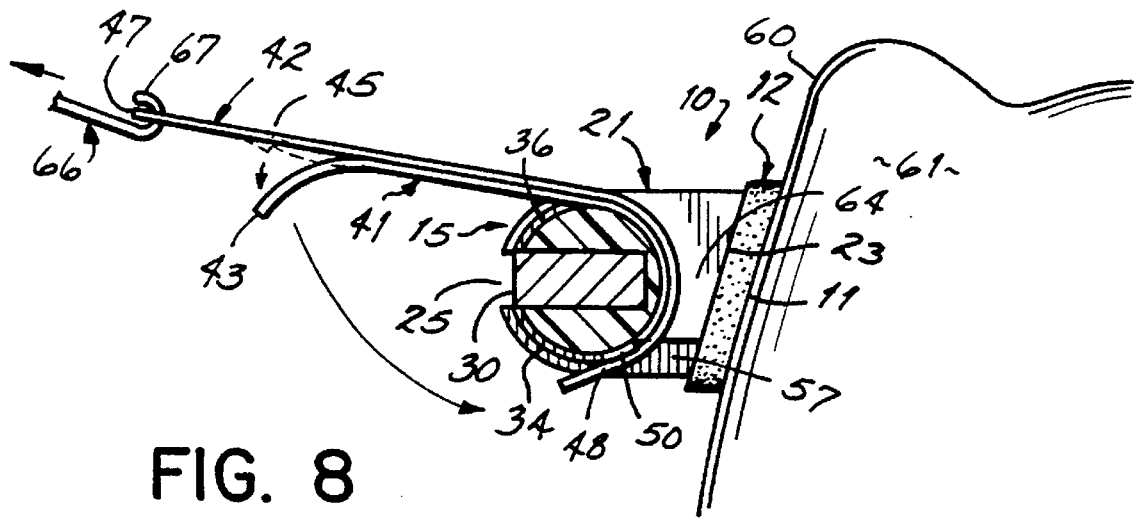
FIG. 8 is a side elevational view, similar to FIG. 6, showing a third step of the preferred embodiment of the method of the invention for ligating an archwire to the bracket.
Figure 9:
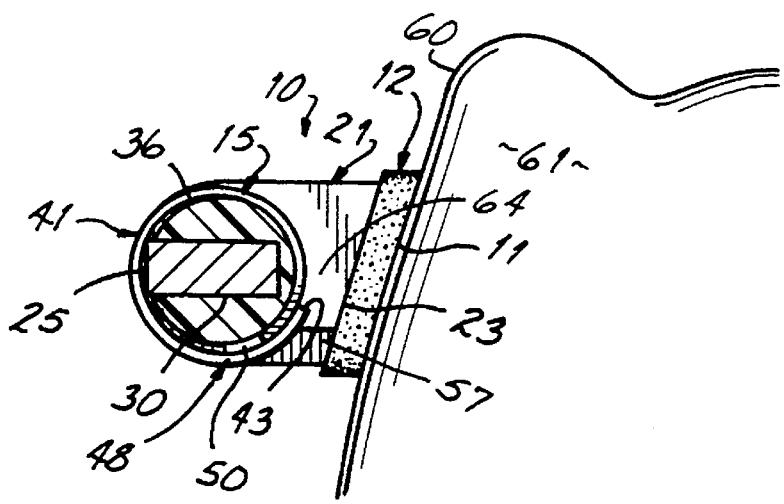
FIG. 9 is a side elevational view, similar to FIG. 6, showing a fourth step of the preferred embodiment of the method of the invention for ligating an archwire to the bracket.

Next, the orthodontist takes a hooked tool, for example as illustrated at 66, and inserts the hooked end 67 thereof through the hole 54, Then, the orthodontist pulls the hook 66 and thus the entire ligature 40 partially through the space 64 until the tabs 50 that form the hooked terminal end 48 are in engagement with the shoulders 57,58, thereby preventing the band 41 from being pulled further through the space 64. Because the diameter of the coil formed by the unstressed ligature is greater than the dimension between the pad 12 and the post 15, the ligature 40 uncoils as it is pulled through the space 64. When the tabs 50 engage the shoulders 57,58 and stop the movement of the band 41, the strip 42 is not so restrained, and therefore, as illustrated in FIG. 8, continues to move through the space 64 such that the forward end 43 of the band 41 drops out of the slot 45 in the strip 42, This allows the strip 42 to be pulled free of the bracket 10 and leaves the band 41 hooked on the bracket 10 to wind itself around the post 15, confining the wire 30 in the slot 25, as illustrated in FIG. 9.

Preferably, the length of the band 41 is such that it makes one complete encirclement of the post 25 with the wire 30 in the slot 25. The strip may, however be less than the circumference of the ligating surface 33, provided that it is constrained about the post 15 to the extend that it is not allowed to uncover the archwire slot 25 to allow the wire 30 to move from the slot 25. The band 41 may also be longer than one circumference of the ligating surface 33 of the post 25, but should not be so long that the forward end 43 thereof extends into the space 64 again or hits the surface of the tooth 61 as the band 41 winds about the post 25.

The band 41, when released by the strip 42, tends to coil a diameter that is less than that of the ligating surface 33 of the post 15, whether the band 41 is of the width designed for engagement with the outer portions 34,35 of the surface 33 or with the smaller diameter inner portion 36 of the surface 33. In either case, the band 41 securely holds the wire 30 in the slot 25. The tieing of the wire 30 to the brackets 10 quick and easy for the orthodontist to accomplish with the assembly and method of the present. The ligated bracket provides a lower profile than the currently used tie-wing brackets of the prior art, giving less interference and a cosmetically improved appliance, that can be hygienically maintained easier than can appliances of the prior art.

From the description above, those skilled in the art will appreciate that various additions and modifications can be made to the jig, and method to connect brackets to teeth with the jig, without departing from the principles of the present invention.

Therefore, the following is claimed:

1. An orthodontic device and ligature combination comprising:

an orthodontic device having a back side thereon adapted to be secured to a tooth of a patient, and a front side including a post having a transverse width and an archwire slot formed longitudinally therein; and a ligature, separate from the bracket, including a band of flat spring-like material configured, when in an unstressed state, to form a coil of a diameter smaller than the transverse width of the post, the band having a forward end, a terminal end and a length, the band being circumferentially moveable, forward end first, around the post, such that, when wrapped around the post, the band will confine an archwire in the slot.

2. The combination of claim 1 wherein:

the device includes a flat pad on the back side thereof having the mounting surface thereon and a support including a pair of spaced legs each extending from a side of the pad on the front side;

the post extends longitudinally between the legs of the support generally parallel to the pad, with the slot extending longitudinally along a side of the post; and the post has an outer surface configured to receive the band of the ligature substantially encircling the post and the archwire slot to hold the archwire in the slot.

3. The combination of claim 1 wherein:

the device includes a support having a pair of spaced legs on the front side thereof;

the post is generally cylindrical in shape, extends between the legs of the support and has an axis generally parallel to the back side of the device, the slot extending along a side of the post generally parallel to the axis; and the post has an outer surface thereon configured to receive the band of the ligature substantially encircling the post and the archwire slot to hold the archwire in the slot.

4. The combination of claim 1 wherein:

the post having a circumference; and the band is dimensioned to encircle the post substantially more than half, but less than one and one half, of the circumference of the post.

5. An orthodontic device and ligature assembly comprising:

an orthodontic device having a back side thereon adapted to be secured to a tooth of a patient, and a front side including a post having a transverse width and an archwire slot formed longitudinally therein;

a ligature including a band of flat spring-like material configured, when in an unstressed state, to form a coil of a diameter smaller than the transverse width of the post, the band having a length such that, when wrapped around the post, the band will confine an archwire in the slot;

the device including a support having a pair of spaced legs on the front side thereof;

the post being generally cylindrical in shape, extending between the legs of the support and having an axis generally parallel to the back side of the device, the slot extending along a side of the post generally parallel to the axis;

the post having an outer surface thereon configured to receive the band of the ligature substantially encircling the post and the archwire slot to hold the archwire in the slot;

the band having a forward end and a hooked terminal end;

the device including a stop, formed on a surface thereof, which, when engaged by the hooked end of the band, prevents movement thereof along the outer surface of the post;

the ligature including a flexible elongated installation strip having a leading end and a trailing end; and the band being removably attached to the strip;

whereby, when the ligature is pulled by the leading end of the strip around the post, the band is pulled around the post until the hooked end of the band engages the stop on the bracket, whereupon the band is released from the strip and left to encircle the post and hold the archwire in the archwire slot.

6. The assembly of claim 5 wherein:

the hooked terminal end of the band includes a pair of sidewardly extending tabs adapted to be engaged by stops on a bracket of the orthodontic appliance when the ligature is pulled around the post.

7. The assembly of claim 5 wherein:

the flexible elongated strip has a handle at the leading end thereof by which the ligature can be engaged and pulled; and the forward end of the band is removably attached to the strip near the forward end thereof.

8. An orthodontic device and ligature combination comprising:

an orthodontic device having a back side thereon adapted to be secured to a tooth of a patient, and a front side including a post having a transverse width and an archwire slot formed longitudinally therein;

at least one ligature selected from a plurality of differently configured ligatures that are separate from the device, each ligature including a band of flat spring-like material configured, when in an unstressed state, to form a coil of a diameter smaller than the transverse width of the post, the band having a length such that; when wrapped around the post, the band will confine an archwire in the slot; and the post having an outer surface formed to receive a selected ligature of the plurality in any one of a plurality of different configurations on the post, each to hold the archwire differently to the device.

9. The combination of claim 8 wherein:

the outer surface of the post is stepped to receive any of a plurality of ligatures of different widths so that each such ligature confines the archwire to a different depth within the archwire slot.

10. The combination of claim 8 wherein:

each configuration of the outer surface is adapted to cooperate with the ligature so as to hold the archwire to a selected degree of tightness in the archwire slot.

11. A device for tying an orthodontic archwire to an orthodontic appliance, the device comprising:

an orthodontic ligature formed of a coiled elongated flat band of spring-like material configured, when in an unstressed state, to form a major portion of a circle, the ligature having a forward end, a terminal end, and a stop formed at the terminal end;

the ligature being wound so as to form a spiral extending outwardly from an inner diameter at the terminal end to an outer diameter at the forward end;

the ligature being adapted such that, when pulled, forward end first, around an orthodontic appliance by the forward end thereof, the stop is engaged by the appliance, and such that when then released, is coiled about the appliance.

12. An orthodontic ligature comprising:

a coiled elongated flat band of spring-like material configured, when in an unstressed state, to form a major portion of a circle, the material having a forward end, a terminal end, and a stop formed at the terminal end;

the material being adapted to be pulled, forward end first, around an orthodontic appliance by the forward end thereof until the stop is engaged by the appliance, and then when released, to coil about the appliance; and the stop including a pair of sidewardly extending tabs formed in the terminal end adapted to be engaged by a surface on a bracket of the orthodontic appliance when the ligature is pulled therearound.

13. A method of ligating an orthodontic archwire to an orthodontic device in the mouth of a patient, the method comprising the steps of:

providing an orthodontic device with an elongated post-like member having a longitudinally extending archwire slot formed therein, the post-like member being supported in spaced relationship with a bonding surface of the device;

bonding the orthodontic device at the bonding surface to a tooth of a patient;

placing an orthodontic archwire in the slot of the device;

providing a ligature of narrow spring-like material which, in an unstressed state, is coiled to a diameter less than the thickness of the post;

at least partially uncoiling the ligature by pulling a leading edge thereof around the post, then releasing the ligature in a position substantially encircling the post and enclosing the archwire in the slot, with the ligature exerting a recoiling force against an outer surface of the post and confines the archwire in the slot.

14. The method of claim 13 wherein:

the ligature includes a flexible elongated strip having a leading end and a trailing end, the forward end of the elongated flat spring-like material being removably attached to the strip;

the uncoiling and pulling step includes the step of pulling the material, forward end first, around the orthodontic device when the strip is pulled therearound by the leading end thereof; and the releasing step includes the step of releasing the material from the strip when the strip is so pulled.

15. An orthodontic ligature comprising:

a coiled elongated flat band of spring-like material configured, when in an unstressed state, to form a major portion of a circle, the material having a forward end, a terminal end, and a stop formed at the terminal end;

the material being adapted to be pulled, forward end first, around an orthodontic appliance by the forward end thereof until the stop is engaged by the appliance, and then when released, to coil about the appliance; and a flexible elongated strip having a leading end and a trailing end; and the forward end of the elongated flat spring-like material being removably attached to the strip;

whereby the material is pulled, forward end first, around an orthodontic appliance when the strip is pulled therearound by the leading end thereof, and is released from the strip when the strip is so pulled and the stop is engaged by the appliance.

16. The ligature of claim 15 wherein:

the flexible elongated strip has a handle at the leading end thereof;

the forward end of the elongated flat spring-like material being removably attached to the strip near and rearward of the forward end thereof.

* * * * *